United States Patent [19]

Korzun

[11] 4,332,726

[45] Jun. 1, 1982

[54] PURIFICATION OF MERCAPTOACYL AMINO ACIDS

[75] Inventor: John N. Korzun, North Brunswick, N.J.

[73] Assignee: E. R. Squibb & Sons, Inc., Princeton, N.J.

[21] Appl. No.: 180,790

[22] Filed: Aug. 25, 1980

[51] Int. Cl.$^3$ ........................................... C07D 207/16
[52] U.S. Cl. .................................... 548/533; 424/274; 548/403; 548/523
[58] Field of Search ..................................... 260/326.4

[56] References Cited

U.S. PATENT DOCUMENTS 4,105,776 8/1978 Ondetti et al. ...................... 424/274
4,154,935 5/1979 Ondetti et al. ...................... 424/274

FOREIGN PATENT DOCUMENTS 2028327 3/1980 United Kingdom ............. 260/326.4

Primary Examiner—Mary C. Lee
Attorney, Agent, or Firm—Lawrence S. Levinson; Stephen B. Davis

[57] ABSTRACT

A method of purifying by separation of mercaptoacyl amino acid from mercaptoacyl amino acid dimer comprising,
  providing a first solution of impure mercaptoacyl amino acid in a fluid container means,
  contacting said first solution with a metal whereby said mercaptoacyl amino acid precipitates yielding a second solution and a purified mercaptoacyl amino acid precipitate,
  separating said purified mercaptoacyl amino acid precipitate from said second solution.

5 Claims, No Drawings

PURIFICATION OF MERCAPTOACYL AMINO ACIDS

BACKGROUND OF THE INVENTION

This invention relates to purification of mercaptoacyl amino acids. Exemplary of acids useful for purification by the method of the present invention are those disclosed by Ondetti et al., in U.S. Pat. Nos. 4,105,776 and 4,154,935 and in U.K. patent application No. GB 2028327 A. The mercaptoacyl amino acid of the Ondetti et al. disclosures are useful as hypotensive agents through their inhibition of angiotensin converting enzyme.

SUMMARY OF THE INVENTION

A method of purifying by separation of mercaptoacyl amino acid from mercaptoacyl amino acid dimer comprising, providing a first solution of impure mercaptoacyl amino acid in a fluid container means, contacting said first solution with a metal whereby said mercaptoacyl amino acid precipitates yielding a second solution and a purified mercaptoacyl amino acid precipitate, separating said purified mercaptoacyl amino acid precipitate from said second solution.

DETAILED DESCRIPTION OF THE INVENTION

The compounds purified here are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g. rats and dogs. (See Biochemistry Vol. 16 No. 25. 1977 pp 5484–5491.) The hypotensive agents intervene in the angiotensinogen→(renin)→angiotensin I→(ACE)angiotensin II sequence by inhibiting angiotensin converting enzyme and reducing or eliminating the formation of the pressor substance angiotensin II. Thus by the administration of one or a combination of the hypotensive agents angiotensin dependent hypertension in the species of mammal suffering therefrom is alleviated. A single dose, or preferably two to four divided daily doses, provided on a basis of about 0.1 to 100 mg of hypotensive agent per kilogram of body weight per day, preferably about 1 to 15 mg per kilogram of body weight per day is appropriate to reduce blood pressure. The composition is administered orally or preferably, parenteral routes such as the subcutaneous, intramuscular, intravenous or intraperitoneal routes can also be employed.

The present method of purifying mercapto acyl amino acids achieves purification by binding with metal ions to form a precipitate.

The precipitate is separated, washed and dried.

The purified precipitate of the present invention comes out of solution at concentrations well below saturation.

The impurity removed by the method of the present invention is mercaptoacyl amino acid dimer. Sulfur to sulfur bonding occurring at room temperature forms mercaptoacyl amino acid dimer.

By the present invention the dimer is converted back to the monomeric form with corresponding enhancement of hypotensive potency.

By contacting the impure mercaptoacyl amino acid with bivalent metal, such as zinc, cadmium, strontium, barium, beryllium or mercury, the metal combines with the dimer.

Each metal ion associates with a single mercaptoacyl amino acid molecule. In so doing the dimers are separated, leaving purified mercapto amino acid in association with bivalent metal ion.

EXAMPLE 1

A glass column one inch in diameter three inches long was filled with a granular zinc from Superior Zinc Corp. Grade No. SZ400 (<20 mesh). A glass reservoir was connected to a pump and then to the column with a recycle line back to the reservoir from the column.

A mixture of 134 grams of 1-(D-3-Mercapto-2-methyl-1-oxopropyl)-L-proline (S,S) containing some 1,1'-[Dithiobis(D-2-methyl-1-oxopropane-3,1-diyl)]bis[L-proline], (S,S,S,S,) was added to 2 liters of distilled water. The pH was adjusted to 0.9–1.1 with concentrated hydrochloric acid. All the solids did not dissolve. The undissolved solids were filtered off and the wet weight was 6.1 grams. The clear solution was fed to the column and recycled but not before some zinc powder fines were first filtered off. After and during 15 minutes of feed and recycle of column effluent a white precipitate forms in the column and is carried over in the column effluent. This white compound is filtered off, washed with water and dried. To yield (S)-1-(3-Mercapto-2-methyl-1-oxopropyl)-L-proline, zinc salt (1:1) having the following properties.

Melting Point and DTA

The compound did not melt in a standard Hoover melting point apparatus at over 250° C. A DTA curve shows a single endotherm at 374° C. without melting.

IR Analysis

IR curve in KBr shows no SH group and shows peaks corresponding to a COO− function.

Solubility

The compound is insoluble in most solvents used in the laboratory including alcohols, esters, chlorinated solvents (i.e., methylene chloride), DMF, DMSO, acetone, amongst others. It is soluble in water only at pHs lower than about 1.6 and greater than 8.0. Dissolving the compound in water at alkaline pH and allowing it to stand, the clear solution would show a milky precipitate.

What is claimed is:

1. A method of separating 1-(D-3-mercapto-2-methyl-1-oxopropyl)-L-proline, (S,S) from an acidic solution containing 1-(D-3-mercapto-2-methyl-1-oxopropyl)-L-proline (S,S) and 1,1'-[dithiobis(D-2-methyl-1-oxopropane-3,1-diyl)]bis[L-proline], (S,S,S,S) comprising treating said acidic solution with a bivalent metal ion selected from the group consisting of zinc, cadmium, strontium, barium, beryllium, and mercury to form a precipitate of 1-(D-3-mercapto-2-methyl-1-oxopropyl)-L-proline, (S,S) bound with said metal ion, and then treating said precipitate to liberate said 1-(D-3-mercapto-2-methyl-1-oxopropyl)-L-proline, (S,S) free of its dimer.

2. The method of claim 1 wherein said acidic solution is an aqueous solution of a pH of 0.9 to 1.1.

3. The method of claim 1 wherein said bivalent metal is in the form of a powder.

4. The method of claim 1 wherein said bivalent metal is in the form of a solution.

5. The method of claim 1 wherein said bivalent metal is zinc.

* * * * *